US009968328B2

(12) United States Patent
Murray

(10) Patent No.: US 9,968,328 B2
(45) Date of Patent: May 15, 2018

(54) WIRELESS DATA TRANSFER IN A DETERMINISTIC ROTATING SYSTEM

(71) Applicant: General Electric Company, Schenectady, NY (US)

(72) Inventor: Donald Murray, West Bend, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 384 days.

(21) Appl. No.: 14/623,936

(22) Filed: Feb. 17, 2015

(65) Prior Publication Data

US 2016/0235387 A1 Aug. 18, 2016

(51) Int. Cl.
*A61B 6/00* (2006.01)
*A61B 6/03* (2006.01)
*H01F 38/18* (2006.01)

(52) U.S. Cl.
CPC .............. *A61B 6/547* (2013.01); *A61B 6/032* (2013.01); *A61B 6/56* (2013.01); *H01F 38/18* (2013.01)

(58) Field of Classification Search
CPC ........... A61B 6/547; A61B 6/56; A61B 6/032; H04B 1/40; H01F 38/18
See application file for complete search history.

(56) References Cited

U.S. PATENT DOCUMENTS 4,796,183 A * 1/1989 Ermert ..................... A61B 6/56 378/10
5,208,581 A 5/1993 Collins
5,577,026 A 11/1996 Gordon et al.
6,141,567 A 10/2000 Youssefmir et al.
6,914,957 B2 7/2005 Dafni et al.
7,043,114 B2 5/2006 Popescu
7,957,786 B2 * 6/2011 Katcha ..................... A61B 6/56 336/145
8,040,278 B2 10/2011 Maltsev et al.

OTHER PUBLICATIONS

Liao et al., Channel Characteristics of MIMO-WLAn communicaitons of 60 GHz for various corridors, EURASIP Journal on Wireless Communications and Networking, 2013, vol. 96, 11 pages.

* cited by examiner

*Primary Examiner* — Courtney Thomas
(74) *Attorney, Agent, or Firm* — Fletcher Yoder, P.C.

(57) ABSTRACT

A system is described herein. The system includes a first transceiver mounted on a rotating assembly arranged on an axis, and a semi-echoic corridor mounted on a stationary assembly which is arranged proximate to the rotating assembly and arranged on the axis, wherein the semi-echoic corridor comprises a slot configured to accommodate the first transceiver of the rotating assembly. The system also includes a second transceiver arranged on the stationary assembly, wherein the first and second transceivers enable wireless communication between the rotating assembly and the stationary assembly.

20 Claims, 4 Drawing Sheets

101
102
106
104
108A
118
108B
120
114
118
112
116
110

100

300

WIRELESS DATA TRANSFER IN A DETERMINISTIC ROTATING SYSTEM

BACKGROUND OF THE INVENTION

Medical imaging systems may include multiple modality units, such as computed tomography (CT), used to generate images of a region of interest of a patient. The system may include a stationary assembly and a rotating assembly, where the rotatable assembly is to rotate about a bore of the stationary assembly. In this manner, image scans may be obtained at a variety of views around a patient located within the bore.

A tremendous amount of scan data is transferred from the rotating assembly to the stationary assembly during a scan. This, the scan data may require a high bandwidth transmission technique. Scan data can be lost due to the speed of rotation during a scan, or the relative motion during the scan. Further, electromagnetic interference may cause latency and fluctuations in the data throughput, and can also result in the corruption of data.

SUMMARY OF THE INVENTION

An embodiment relates to a system. The system includes a first transceiver mounted on a rotating assembly arranged on an axis, and a semi-echoic corridor mounted on a stationary assembly which is arranged proximate to the rotating assembly and arranged on the axis, wherein the semi-echoic corridor comprises a slot configured to accommodate the first transceiver of the rotating assembly. The system also includes a second transceiver arranged on the stationary assembly, wherein the first and second transceivers enable wireless communication between the rotating assembly and the stationary assembly.

Another embodiment relates to an imaging system. The imaging system includes a gantry, a first transceiver, a second transceiver, and a semi-echoic corridor. The gantry includes a rotating assembly and a stationary assembly arranged proximate to each other about a bore along an imaging axis. The first transceiver is mounted on the rotating assembly, and a semi-echoic corridor is mounted on the stationary assembly. The semi-echoic corridor includes a slot configured to accommodate the first transceiver of the rotating assembly. The second transceiver is arranged on the stationary assembly, where the first and second transceivers enable wireless communication between the rotating assembly and the stationary assembly.

Still another embodiment relates to a method. The method includes rotating a rotating assembly of a system through axial positions of a complete rotation beginning at a zero degree position, wherein the rotating assembly comprises a first transceiver. The method also includes performing beam searching between the first transceiver of the rotating assembly and a second transceiver arranged in a stationary assembly of the system at each axial position until communication is established between the first transceiver and the second transceiver at each of the axial positions. Additionally, the method includes performing beam tracking at each axial position when communication is established between the first and second transceivers at each axial position to optimize data transmission and generate beamforming parameters at each axial position. Moreover, the method includes storing, for each of the first transceiver and the second transceiver, axial position information and corresponding beamforming parameters for each axial position in a non-volatile memory.

Yet another embodiment relates to a non-transitory computer-readable medium. The non-transitory computer-readable medium has stored thereon a computer program comprising instructions which when executed by a computer cause the computer to rotate a rotating assembly of a system through axial positions of a complete rotation beginning at a zero degree position, wherein the rotating assembly comprises a first transceiver, The instructions may also cause the computer to perform beam searching between the first transceiver of the rotating assembly and a second transceiver arranged in a stationary assembly of the system at each axial position until communication is established between the first transceiver and the second transceiver at each of the axial positions. Additionally, the instructions cause the computer to perform beam tracking at each axial position when communication is established between the first and second transceivers at each axial position to optimize data transmission and generate beamforming parameters at each axial position. Moreover, the instructions cause the computer to store, for each of the first transceiver and the second transceiver, axial position information and corresponding beamforming parameters for each axial position in a non-volatile memory. Finally, the instructions cause the computer to retrieve the beamforming parameters for each axial position from the memory for subsequent rotations of the rotating assembly.

BRIEF DESCRIPTION OF THE DRAWINGS

The present techniques will become more fully understood from the following detailed description, taken in conjunction with the accompanying drawings, wherein like reference numerals refer to like parts, in which.

In some cases, the same numbers are used throughout the disclosure and the figures to reference like components and features. Numbers in the 100 series refer to features originally found in FIG. 1; numbers in the 200 series refer to features originally found in FIG. 2; and so on.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Modern CT scanners gather a large amount of data during normal operation. For example, scan data throughput requirements of a medical imaging system may be in excess of 40 Gigabits per second (Gb/s). One of the challenges in x-ray computed tomography (CT) is the need to transfer this tremendous amount of scan data from a rotating assembly to a stationary assembly. Existing solutions cannot reliably meet the high throughput requirements of a modern CT scanner without bulky, expensive systems. Typically, as data throughput increases, so does the size and cost of the medical imaging system.

The present techniques provide a low cost, robust alternative to traditional wireless solutions. It enables a stable, deterministic electromagnetic environment in which wireless signals will propagate with minimal signal degradation. In embodiments, upon initial power up the system "self-calibrates" to determine the radiation patterns as a function of multiple rotational positions, stores them in non-volatile memory, and then retrieves them later during actual scans. A technical effect of the present techniques is transferring wireless signals with little to no signal degradation. Further, a technical effect of the present techniques is efficient signal transfer in light of the relative motion between transmitter and receiver in a modern scanner. Additionally, the mechanical components of the design do not require tight tolerances, and the electronic assemblies can be implemented using transceiver components that are currently available for consumer products. Accordingly, although a transmitter and receiver may be described, the present techniques may be implemented with a transceiver.

Figure 1:
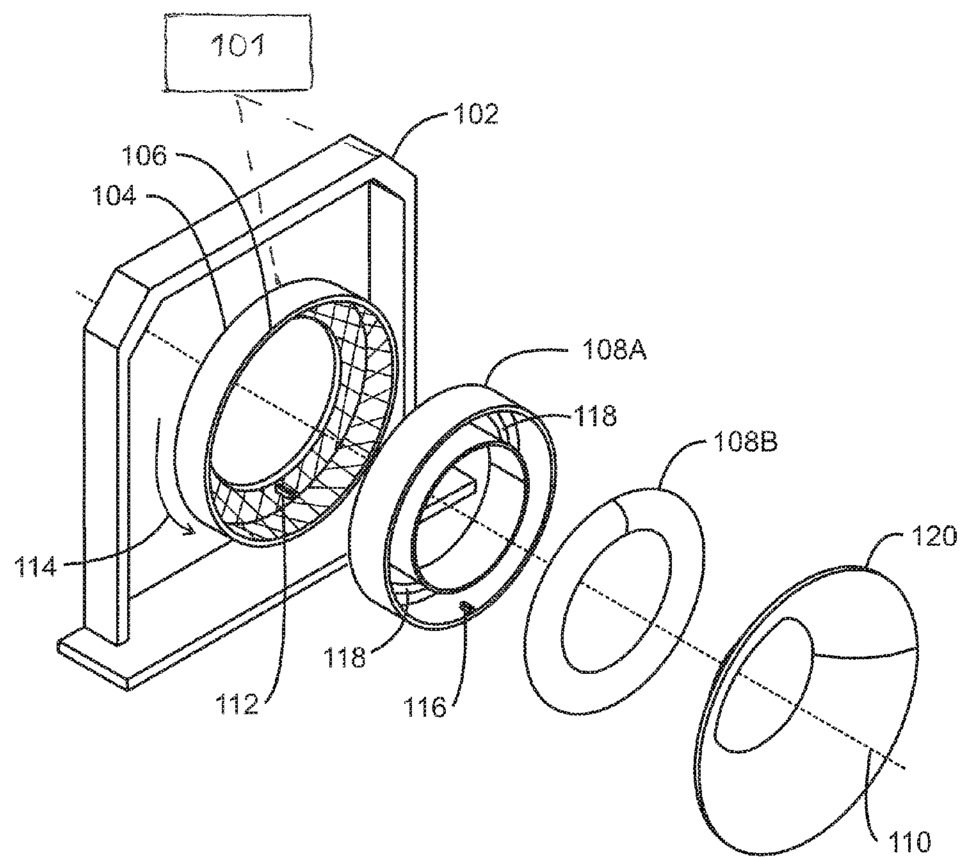
FIG. 1 is an exploded diagram of a medical imaging system.

FIG. 1 is an exploded diagram of a medical imaging system 100. In embodiments, the medical imaging system 100 is a CT system. The medical imaging system 100 includes a stationary assembly 102. In embodiments, the stationary assembly may be a stationary frame. A rotating assembly 104 rotates on a bearing connected to the stationary assembly 102. The rotating assembly and the stationary assembly may be located within a gantry and arranged proximate to each other about a bore along an imaging axis. The rotating assembly 104 includes a lip 106 that extends over the outside of a semi-echoic corridor, where the semi-echoic corridor includes item 108A and item 108B. The rotating assembly 104 rotates about the z-axis 110 of the system 100. In embodiments, the rotation occurs about the z-axis, as illustrated by the arrow 114. The rotational position of the rotating assembly 104 is deterministic due to the presence of an axial encoder in the medical imaging system 100, where the rotational position from the axial encoder is made available to other system components over a real-time communication network.

In embodiments, the medical imaging system 100 is located within a gantry. Within the gantry may be a network of individual computers, each with specialized functions within the gantry as a part of the communication network. In embodiments, the network may be a Serial Rapid Input/Output (SRIO) network. In examples, one computer may include a controller 101 that obtains data from the axial encoder such that each image obtained is annotated with some information about where in the system the detector was at the time the image was obtained. This encoding data is then used to reconstruct the 3D images of the scan.

Portions of the rotating assembly 104 may be covered with an electromagnetically attenuative material. This is illustrated with cross-hatching in FIG. 1. For example, the side of the rotating assembly 104 facing the semi-echoic corridor 108A as well as a lip overhanging the semi-echoic corridor 108A is covered with the electromagnetically attenuative material. The electromagnetically attenuative material may be any material capable of absorbing any electromagnetic energy. In embodiments, the cross-hatching may illustrate an electromagnetically reflective material. The electromagnetically reflective material may be any material capable of reflecting electrical signals within the semi-echoic corridor.

A wireless transmitter 112 is mounted on the rotating assembly 104 at some radial distance from the axis of rotation 110. This transmitter 112 also has a physical connection to the communication network in the medical imaging system 100 in order to retrieve real-time axial position data. The semi-echoic corridor 108A and 108B is mounted to the stationary assembly 102. In embodiments, the semi-echoic corridor is formed from metal. For example, the metal may be aluminum. The top portion of the semi-echoic corridor 108B completes the enclosure of the semi-echoic corridor 108A when the medical imaging system 100 is fully assembled. Although not illustrated, the inside wall of the top portion 108B of the semi-echoic corridor 108A may also be covered an electromagnetically reflective material or electromagnetically attenuative material. Accordingly, the interior walls of the semi-echoic corridor, including both items 108A and 108B, include an electromagnetically attenuative material or electromagnetically reflective material.

A wireless receiver 116 is mounted inside the semi-echoic corridor 108A. The receiver 116 also has a physical connection to the communication network in the medical imaging system 100 in order to retrieve real-time axial position data. A slot 118 in the semi-echoic corridor 108A enables the antennas on the transmitter 112 to transmit inside the corridor to the wireless receiver 116 while the rotating assembly 104 rotates about the z-axis 110. In embodiments, the wireless communication comprises spatially multiplexed wireless communication. A horn-shaped cover 120 may complete the medical imaging system 100 enclosure, shown for reference. In embodiments, the semi-echoic corridor 108A is formed from an inner cylinder and an outer cylinder. The slot 118 of the semi-echoic corridor may be arranged between the inner cylinder and the outer cylinder. The second transceiver may be mounted on the outer cylinder, and the semi-echoic corridor may further comprise a cover 108B.

Moreover, in embodiments the wireless transmitter 112 is a first transceiver, and the wireless receiver 116 is a second transceiver. Accordingly, the first transceiver may be mounted on the rotating assembly 104 at some radial distance from the axis of rotation. The semi-echoic corridor 108A and 108B may be mounted on a stationary assembly, such as the stationary assembly 102, which is arranged proximate to the rotating assembly 104 and arranged on the axis 110. As illustrated in FIG. 1, the semi-echoic corridor 108A and 108B includes a slot 118 configured to accommodate the first transceiver 112 of the rotating assembly. The first and second transceivers may enable wireless communication between the rotating assembly and the stationary assembly. A controller 101 may be communicatively coupled to the rotating assembly and to the stationary assembly via a network. In some embodiments, the network is a real-time network. The controller 101 may retrieve axial position data that is stored at a location connected to the network. During operation of the medical imaging system 100, the controller 101 may retrieve axial position data and beamforming parameters to be applied to the first transceiver and/or the second transceiver. In embodiments, the controller 101 can be any processing component that retrieves axial position data or beamforming parameters.

The semi-echoic corridor provides an ideal, isolated environment in which the wireless signals may propagate, eliminating any electromagnetic interference. Electromagnetic interference may result in latency, fluctuations in data throughput, or corruption of data within the medical imaging system 100. Moreover, the isolated environment of the semi-echoic corridor enables signal reflections of the wireless data transmitted in the corridor. Spatial multiplexing is used to take advantage of the signal reflection that occurs within the semi-echoic corridor. In non-spatially-multiplexed systems, the signal reflections that occur in this corridor would cause interference due to multipath fading.

In spatial multiplexing, multiple data signals are transmitted at the same time. The data signals are transmitted on the same channel, but by a different antenna. The medical imaging system 100 includes multiple antennas on the transmitter 112 and multiple antennas on the receiver 116. Through spatial multiplexing, data is split evenly then amongst the multiple antennas and then transmitted across the multiple antennas. In embodiments, no antenna of the multiple antennas of the transmitter transmits the same data. At the receiver, the multiple antennas of the receiver receive various portions of the plurality of transmitted signals. A signal processing algorithm is used to decode the signals and combine them into the original transmitted signal. Spatial multiplexing results in an increase of wireless data throughput when compared to other transmission techniques, such as spatial diversity.

Phased array antennas enable beamforming to be applied to the wireless signals. Using phased array antennas on the transceivers, spatial multiplexing creates numerous parallel signals operating on the same channel, with each signal carrying a portion of the data transmission. The parallel signals reflect off of objects in the environment until they arrive at the receiving antenna array. A signal processing algorithm is used to decode the various reflected signals at the receiver and recover the original data transmission. Spatial multiplexing uses dynamic beamforming to optimize the data transmission. By optimizing the data transmission, fluctuations in data throughput may be eliminated. Moreover, by optimizing the data throughput, fluctuations in data latency and throughput over time resulting from the high relative velocity between transceivers as the radiation pattern of the signal changes is eliminated.

The medical imaging system 100 can implements dynamic beamforming during a self-calibration of the system. Dynamic beamforming consists of two functions: beam searching and beam tracking. In beam searching, a handshaking algorithm is used to establish communication between transceivers at system startup, or in the event of loss of signal during normal operation. In beam tracking, data transfer is optimized via an algorithm whereby the transceivers adjust various antenna parameters to modify the wireless radiation pattern until both transceivers "agree" that the data transfer is optimized. An agreement that data transfer is optimized may include meeting various data transfer requirements.

Figure 2:
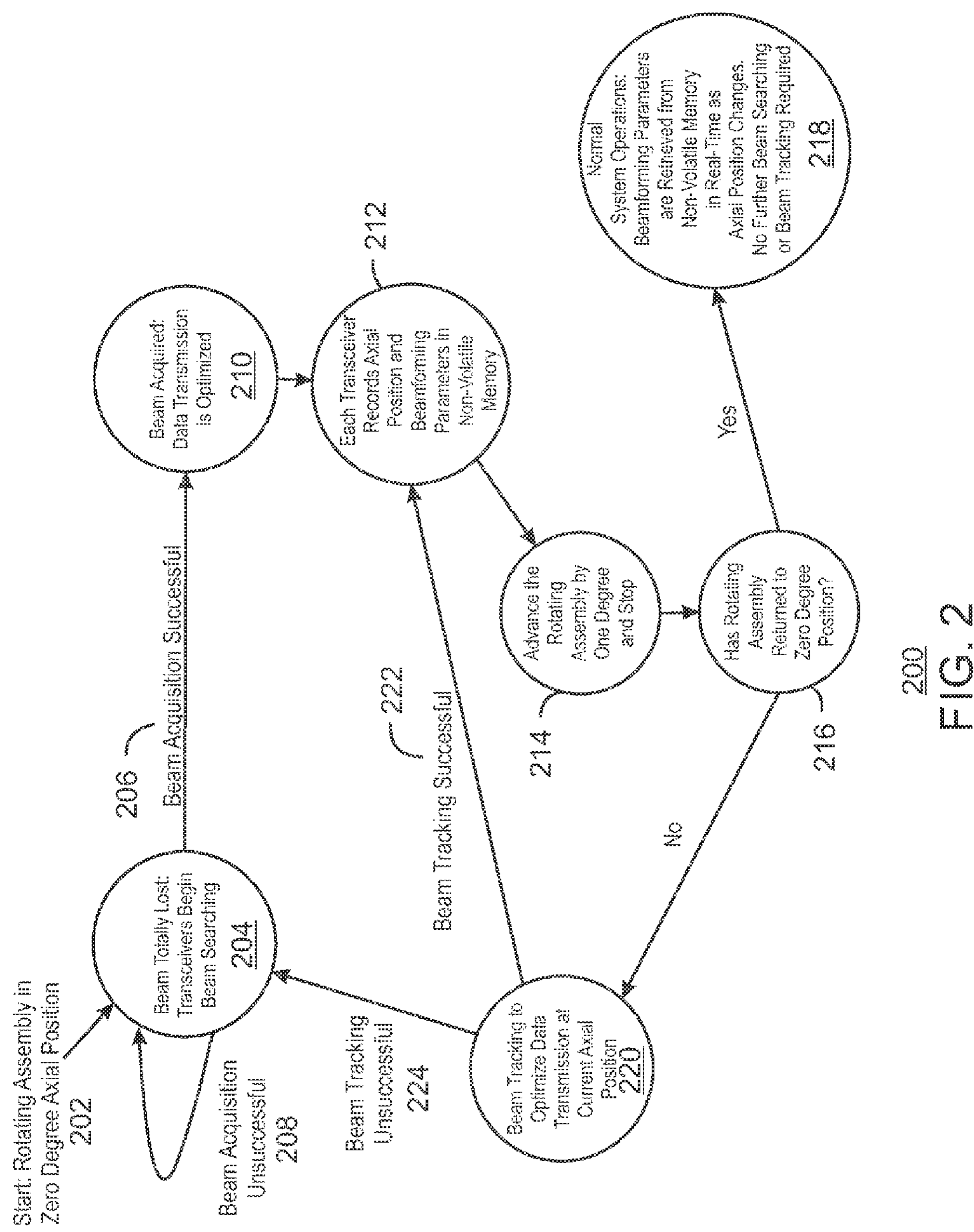
FIG. 2 is a flow diagram on self calibration of wireless beamforming parameters in a deterministic rotating system.

FIG. 2 is a flow diagram of self calibration of wireless beamforming parameters in a deterministic rotating system. At block 202, upon startup of the medical imaging system, before any scan data is transmitted, the rotating assembly is placed at the zero degree axial position. At this point, the beams that transmit scan data are considered "lost," as there are no parameters available to be applied to the beams in order to optimize data transmission. The beams may also be considered lost when the parameters are outdated due to a change in configuration of the system, or due to environmental changes. A change in configuration may occur when the system is powered off, or when the system is altered for a repair or addition to the system. At block 204, the transceivers perform beam searching until communication is established. When beam acquisition is successful at reference number 206, process flow continues to block 210. When beam acquisition is unsuccessful at reference number 208, process flow remains at block 204 where beamforming is performed again.

At block 210, data transmission optimization is performed, and process flow continues to block 212. Data transmission optimization is used to determine beamforming parameters to apply at the particular axial position of the transceivers. The beamforming parameters may be used to apply weights to the signals of the antennas. The weights may be the complex weighting factor having a magnitude and a phase. In embodiments, the parameters determined in self-calibration, during system power up, and are not programmed or stored during the manufacture of the system. At block 212, each transceiver records axial position and beamforming parameters in non-volatile memory for the current rotational position of the rotating assembly. At block 214, the rotating assembly is advanced by one degree. Although the present techniques are described as rotating by one degree, the rotating assembly may rotate by any number of degrees to arrive at various positions during self calibration. At block 216, it is determined if the rotating assembly has returned to the zero degree axial position. If the rotating assembly has returned to the zero degree axial position, process flow continues to block 218. If the rotating assembly has not returned to the zero degree axial position, process flow continues to block 220. At block 218, normal system operations can begin. In particular, beamforming parameters can be retrieved from non-volatile memory in real-time as the axial position changes. For example, beamforming parameters can be retrieved from non-volatile memory in real-time as the axial position changes during a scan. No further beam searching or beam tracking is required.

At block 220, beam tracking is performed to optimize data transmission at the current axial position. If the beam tracking is successful at reference number 222, process flow returns to block 212. If the beam tracking is unsuccessful at reference number 224, process flow returns to block 204. In this manner, the rotating assembly is rotated and stopped at numerous axial positions throughout the full 360 degrees of rotation. At each position, beam tracking is performed until the data transmission is optimized. The transmitter, receiver, or transceiver, retrieves the current axial position from the medical imaging system network, and then this position and the optimal antenna parameter values are stored in a lookup table in non-volatile memory. Once the self-calibration is complete, no further beam tracking is necessary during the course of normal operations. During normal operation of the medical imaging system, the transmitter, receiver, or transceiver, receive continuous axial position data over the network in real-time, and they dynamically set their antenna parameters to the corresponding values in the lookup table. The signal is always optimized, with no intermittent throughput reduction, latency, or data corruption.

Figure 3:
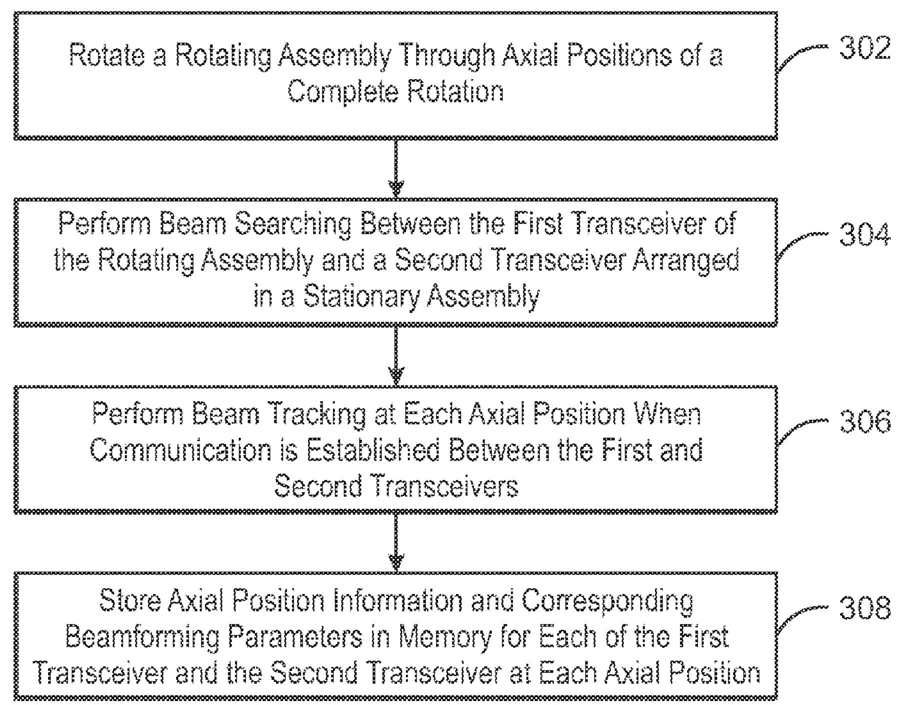
FIG. 3 is a process flow diagram for wireless data transfer in a deterministic rotating system.

FIG. 3 is a process flow diagram 300 for wireless data transfer in a deterministic rotating system. At block 302, a rotating assembly of a system is rotated through axial positions of a complete rotation beginning at a zero degree position, wherein the rotating assembly comprises a first transceiver. In embodiments, the rotating assembly is rotated by advancing and stopping rotation of the rotating assembly by one degree until the rotating assembly has a returned to the zero degree position.

At block 304, beam searching is performed between the first transceiver of the rotating assembly and a second transceiver arranged in a stationary assembly of the system at each axial position until communication is established between the first transceiver and the second transceiver at each of the axial positions. At block 306, beam tracking is performed at each axial position when communication is established between the first and second transceivers at each axial position to optimize data transmission and generate beamforming parameters at each axial position. The beam searching and the beam tracking may be performed for each degree of rotation of the rotating assembly. At block 308, axial position information and corresponding beamforming parameters may be stored for each of the first transceiver and the second transceiver at each axial position in a memory. The beamforming parameters may be retrieved for each axial position from the memory for subsequent rotations of the rotating assembly.

Figure 4:
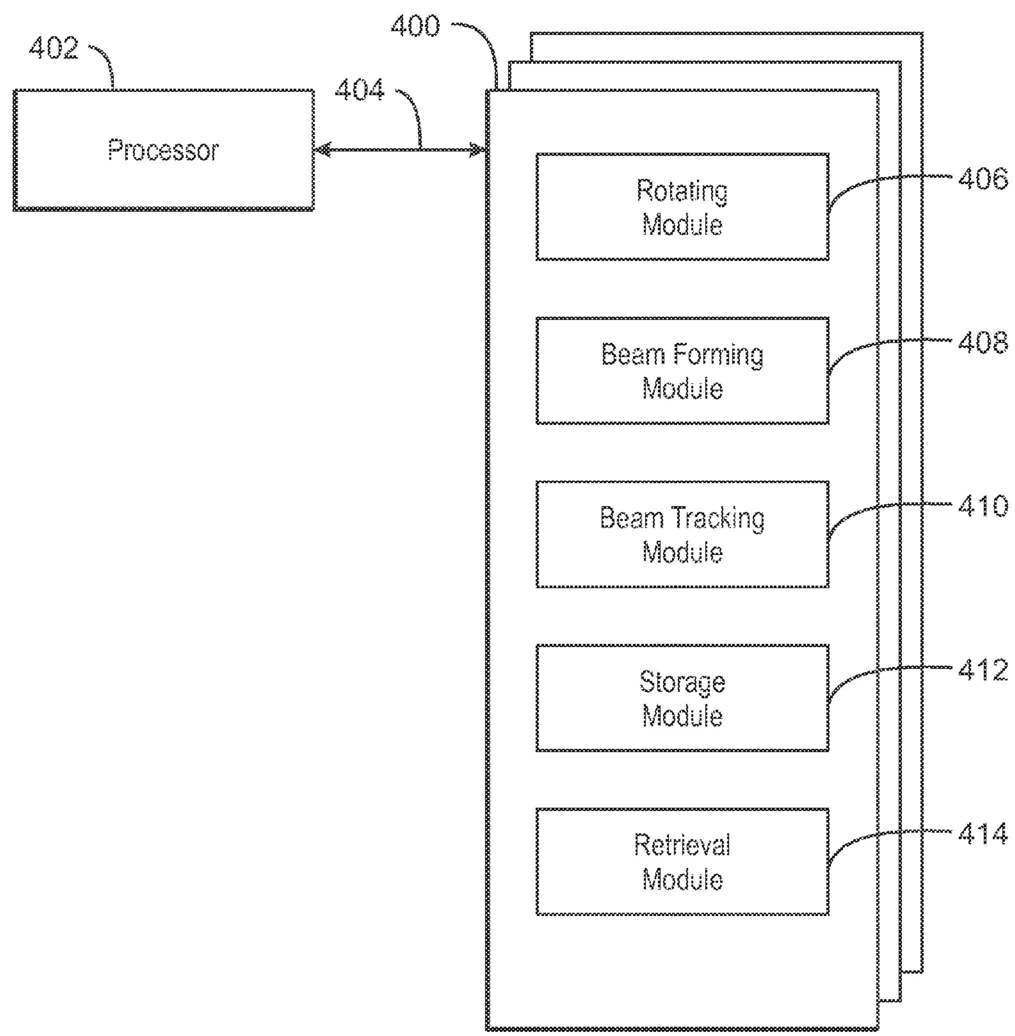
FIG. 4 is a block diagram showing tangible, non-transitory computer-readable media that stores code for data transfer in a deterministic rotating system.

FIG. 4 is a block diagram showing tangible, non-transitory computer-readable media 400 that stores code for data transfer in a deterministic rotating system. The tangible, non-transitory computer-readable media 400 may be accessed by a processor 402 over a computer bus 404. Furthermore, the tangible, non-transitory computer-readable medium 400 may include code configured to direct the processor 402 to perform the methods described herein.

The various software components discussed herein may be stored on one or more tangible, non-transitory computer-readable media 400, as indicated in FIG. 4. For example, a rotating module 406 may be configured to rotate the rotating assembly of a system through axial positions of a complete rotation beginning at a zero degree position, wherein the rotating assembly comprises a first transceiver. A beamforming module 408 may be configured to perform beam searching between the first transceiver of the rotating assembly and a second transceiver arranged in a stationary assembly of the system at each axial position until communication is established between the first transceiver and the second transceiver at each of the axial positions. A beam tracking module 410 may be configured to perform beam tracking at each axial position when communication is established between the first and second transceivers at each axial position to optimize data transmission and generate beamforming parameters at each axial position. A storage module 412 may be configured to store, for each of the first transceiver and the second transceiver, axial position information and corresponding beamforming parameters for each axial position in a memory. A retrieval module 414 may be configured to retrieve the beamforming parameters for each axial position from the memory for subsequent rotations of the rotating assembly.

The block diagram of FIG. 4 is not intended to indicate that the tangible, non-transitory computer-readable media 400 is to include all of the components shown in FIG. 4. Further, the tangible, non-transitory computer-readable media 400 may include any number of additional components not shown in FIG. 4, depending on the details of the specific implementation.

The various embodiments are not limited to medical imaging systems for imaging human subjects, but may include, for example, veterinary systems. As used herein, the term "patient" may refer to a human patient or any other animal.

While embodiments are described herein with respect to modality units used in the medical field, embodiments described herein can encompass those situations in which any modality unit is used in an imaging procedure. Further, those of skill in the art will recognize that the present techniques are applicable to many different hardware configurations, software architectures, organizations, or processes.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system, comprising:

a first transceiver mounted on a rotating assembly arranged on an axis;

a semi-echoic corridor mounted in a stationary position on a stationary assembly which is arranged proximate to the rotating assembly and arranged on the axis, wherein the semi-echoic corridor comprises a slot configured to accommodate the first transceiver of the rotating assembly; and a second transceiver arranged in a stationary position within the semi-echoic corridor;

wherein the first and second transceivers enable wireless communication between the rotating assembly and the stationary assembly, and the first transceiver comprises a transmitter and the second transceiver comprises a receiver.

2. The system of claim 1, further comprising:

a controller communicatively coupled to the rotating assembly and to the stationary assembly via a network.

3. The system of claim 2, wherein the controller provides axial position data to the first transceiver and/or the second transceiver.

4. The system of claim 3, wherein the controller is configured to:

during calibration of the system:

rotate a rotating assembly of the system through axial positions of a complete rotation beginning at a zero degree position, wherein the rotating assembly comprises a first transceiver;

perform beam searching between the first transceiver of the rotating assembly and a second transceiver arranged in a stationary assembly of the system at each axial position until communication is established between the first transceiver and the second transceiver at each of the axial positions;

perform beam tracking at each axial position when communication is established between the first and second transceivers at each axial position to optimize data transmission and generate beamforming parameters at each axial position; and store, for each of the first transceiver and the second transceiver, axial position information and corresponding beamforming parameters for each axial position in a memory; and subsequent to calibration of the system:

retrieve the stored beamforming parameters for each axial position from the memory and utilize the stored beamforming parameters for subsequent rotations of the rotating assembly during scans to acquire image data, wherein utilizing the stored beamforming parameters optimizes data transmission without having to perform beam searching and beam tracking.

5. The system of claim 1, wherein the wireless communication comprises spatially multiplexed wireless communication.

6. The system of claim 1, wherein interior walls of the semi-echoic corridor comprise an electromagnetically reflective material.

7. The system of claim 1, wherein the semi-echoic corridor comprises:

an inner cylinder; and an outer cylinder;

and wherein the slot is arranged between the inner cylinder and the outer cylinder.

8. The system of claim 7 wherein the second transceiver is mounted on the outer cylinder.

9. The system of claim 7, where the semi-echoic corridor further comprises a cover.

10. The system of claim 1, wherein the semi-echoic corridor is formed from metal.

11. The system of claim 1, wherein the transmitter and the receiver are the only transceivers of the system.

12. An imaging system, comprising:

gantry comprising a rotating assembly and a stationary assembly arranged proximate to each other about a bore along an imaging axis;

a first transceiver mounted on the rotating assembly;

a semi-echoic corridor mounted in a stationary position on the stationary assembly, wherein the semi-echoic corridor comprises a slot configured to accommodate the first transceiver of the rotating assembly; and a second transceiver arranged in a stationary position within the semi-echoic corridor;

wherein the first and second transceivers enable wireless communication between the rotating assembly and the stationary assembly, and the first transceiver comprises a transmitter and the second transceiver comprises a receiver.

13. The system of claim 12, further comprising:

a controller communicatively coupled to the rotating assembly and to the stationary assembly via a network.

14. The system of claim 13, wherein the controller provides axial position data to the first transceiver and/or the second transceiver.

15. The system of claim 12, wherein the wireless communication comprises spatially multiplexed wireless communication.

16. The system of claim 12, wherein interior walls of the semi-echoic corridor comprise an electromagnetically reflective material.

17. A method, comprising:

during calibration of an imaging system:

rotating a rotating assembly of the imaging system through axial positions of a complete rotation beginning at a zero degree position, wherein the rotating assembly comprises a first transceiver;

performing beam searching between the first transceiver of the rotating assembly and a second transceiver arranged in a stationary assembly of the imaging system at each axial position until communication is established between the first transceiver and the second transceiver at each of the axial positions;

performing beam tracking at each axial position when communication is established between the first and second transceivers at each axial position to optimize data transmission and generate beamforming parameters at each axial position; and storing, for each of the first transceiver and the second transceiver, axial position information and corresponding beamforming parameters for each axial position in a memory; and subsequent to calibration of the imaging system:

retrieving the stored beamforming parameters for each axial position from the memory and utilizing the stored beamforming parameters for subsequent rotations of the rotating assembly during scans to acquire image data, wherein utilizing the stored beamforming parameters optimizes data transmission without having to perform beam searching and beam tracking.

18. The method of claim 17, wherein rotating the rotating assembly comprises advancing and stopping rotation of the rotating assembly by one degree until the rotating assembly has a returned to the zero degree position.

19. The method of claim 18, wherein the beam searching and the beam tracking are performed for each degree of rotation of the rotating assembly.

20. A non-transitory computer-readable medium having stored thereon a computer program comprising instructions which when executed by a computer cause the computer to:

during calibration of an imaging system:

rotate a rotating assembly of the imaging system through axial positions of a complete rotation beginning at a zero degree position, wherein the rotating assembly comprises a first transceiver;

perform beam searching between the first transceiver of the rotating assembly and a second transceiver arranged in a stationary assembly of the imaging system at each axial position until communication is established between the first transceiver and the second transceiver at each of the axial positions;

perform beam tracking at each axial position when communication is established between the first and second transceivers at each axial position to optimize data transmission and generate beamforming parameters at each axial position; and store, for each of the first transceiver and the second transceiver, axial position information and corresponding beamforming parameters for each axial position in a memory; and subsequent to calibration of the imaging system:

retrieve the stored beamforming parameters for each axial position from the memory and utilize the stored beamforming parameters for subsequent rotations of the rotating assembly during scans to acquire image data, wherein utilizing the stored beamforming parameters optimizes data transmission without having to perform beam searching and beam tracking.

* * * * *